United States Patent [19]

Balitz et al.

[11] 4,360,595
[45] Nov. 23, 1982

[54] FERMENTATION PROCESS FOR PRODUCING ANANDIMYCIN

[75] Inventors: David M. Balitz, Syracuse; James A. Bush, Fayetteville; Frances A. O'Herron, Syracuse; Donald E. Nettleton, Jr., Jordan, all of N.Y.

[73] Assignee: Bristol-Myers Company, New York, N.Y.

[21] Appl. No.: 236,381

[22] Filed: Feb. 20, 1981

[51] Int. Cl.³ .................... C12P 17/18; C12R 1/465
[52] U.S. Cl. .................................... 435/119; 435/886; 549/278
[58] Field of Search .......................... 435/119, 886

[56] References Cited

PUBLICATIONS

Derwent publication 42198c/24, abstracting Japanese Published Patent Application 55/57,586 (1980).
Hatano et al., Agric. Biol. Chem., 44 pp. 1157-1163, 1980.
J. Am. Chem. Soc., vol. 75, pp. 4011 and 4012, (1953).
J. Am Chem. Soc., vol. 80, pp. 1636-1639, (1958).
Helv. Chim. Acta, 43, pp. 58-63, (1960).

*Primary Examiner*—Alvin E. Tanenholtz
*Attorney, Agent, or Firm*—David M. Morse

[57] ABSTRACT

A polycyclic antitumor antibiotic designated herein as anandimycin is produced by fermentation of *Streptomyces anandii* subsp. *araffinosus* strain C-22,437 (ATCC 31431). Anandimycin possesses antibacterial activity and inhibits the growth of tumors in experimental animals.

1 Claim, 2 Drawing Figures

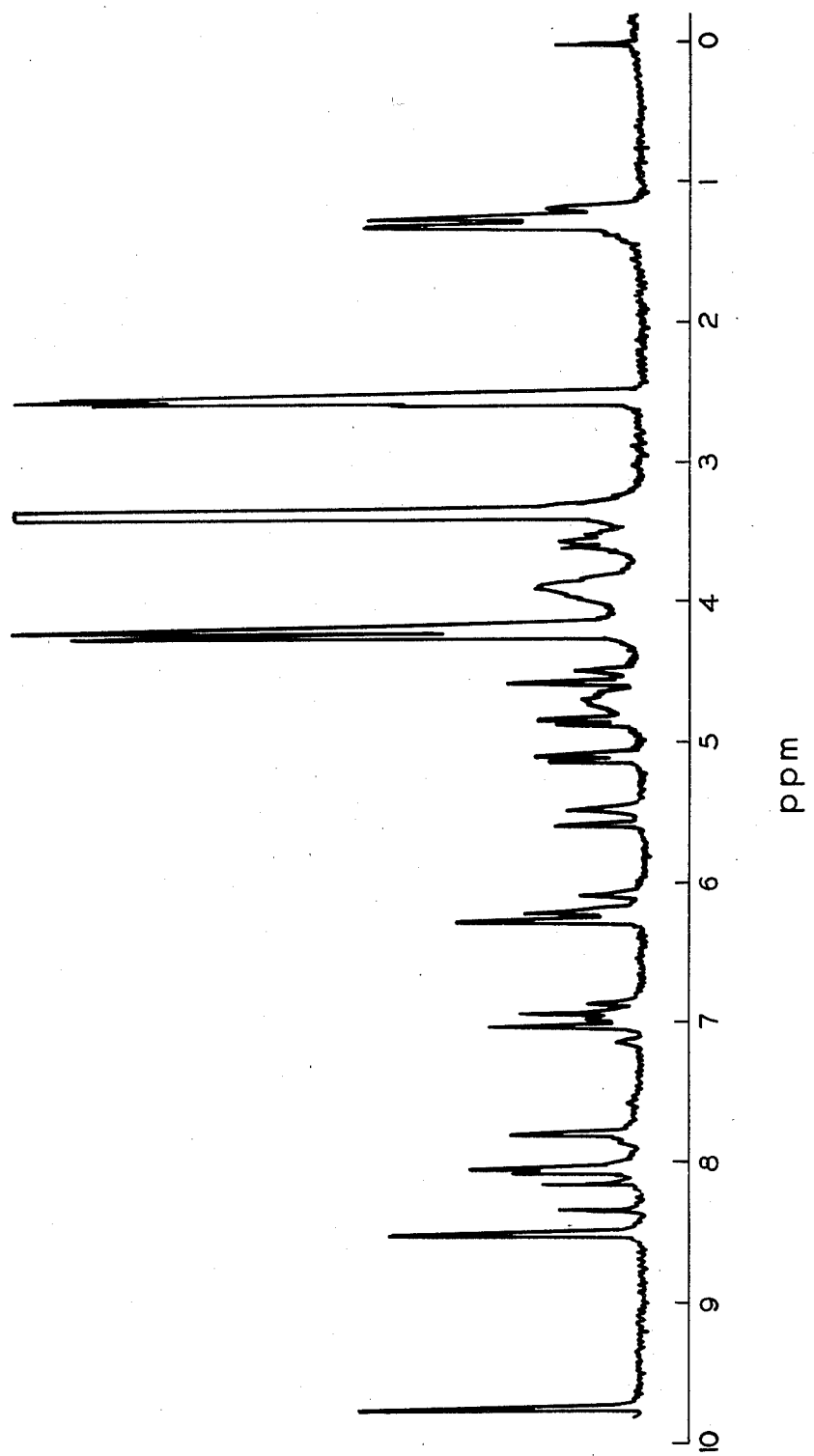

FERMENTATION PROCESS FOR PRODUCING ANANDIMYCIN

BACKGROUND OF THE INVENTION

1. Field of the Invention

The present invention relates to a polycyclic antitumor antibiotic designated herein as anandimycin and to its preparation by fermentation of a new microorganism *Streptomyces anandii* subsp. *araffinosus* strain C-22,437 (ATCC 31431).

2. Description of the Prior Art

Japanese Published Patent Application 55/57,586 discloses an antitumor antibiotic DC-38 (component Ia) of unknown structure which appears to have the same or very similar physicochemical properties to the anandimycin antibiotic of the present invention. Further studies are underway to confirm whether anandimycin is identical with DC-38 Ia.

The antibiotic toromycin disclosed in *Agric. Biol. Chem.* 44 (5):1157–1163 (1980) also appears to have properties identical with or very similar to both anandimycin and DC-38 Ia. As in the case with DC-38 Ia, further studies are underway to establish whether anandimycin and toromycin are the same chemical substance.

Anandimycin is similar to the antibiotic chartreusin disclosed in *J. Amer. Chem. Soc.* 75:4011 (1953), *J. Amer. Chem. Soc.* 80:1636, 1639 (1958) and *Helv. Chim. Acta* 43:58 (1960) in certain of its physicochemical and biological properties. Differences in such properties as elemental analysis, ultraviolet absorption spectrum and molecular weight, however, clearly distinguish these two polycyclic antibiotics.

DESCRIPTION OF THE DRAWINGS

FIG. 2 shows the proton magnetic resonance spectrum of anandimycin in DMSO (100 MHz).

SUMMARY OF THE INVENTION

Figure 1:
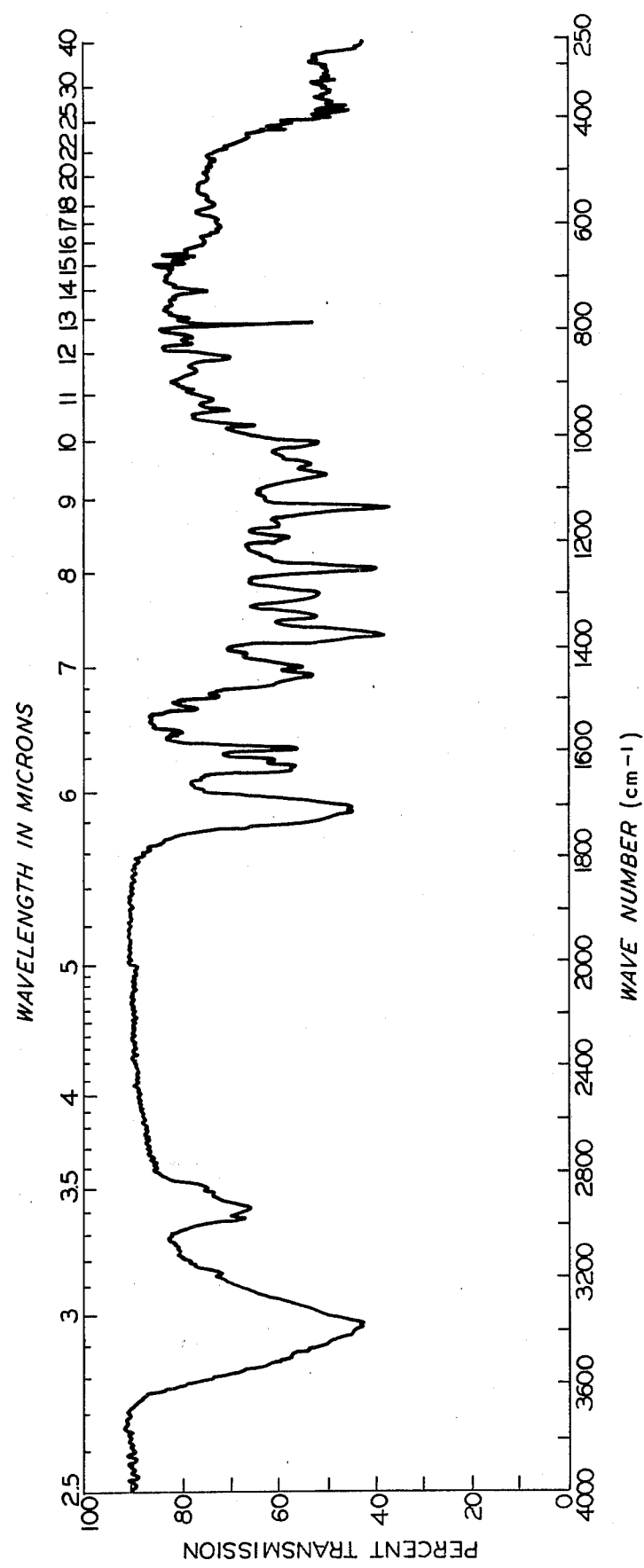
FIG. 1 shows the infrared absorption spectrum of anandimycin when pelleted in potassium bromide.

The present invention provides the polycyclic antibiotic anandimycin and a process for its preparation and isolation in a purified state free of co-produced substances. The antibiotic is obtained by cultivating an anandimycin-producing strain of *Streptomyces anandii* subsp. *araffinosus* having the identifying characteristics of ATCC 31431 in an aqueous nutrient medium containing assimilable sources of carbon and nitrogen under submerged aerobic conditions until a substantial amount of anandimycin is produced by said organism in said culture medium and then recovering the anandimycin from said culture medium substantially free of co-produced substances.

Anandimycin has been found to exhibit antimicrobial activity and to inhibit the growth of tumors in experimental animals.

DETAILED DESCRIPTION

The anandimycin antibiotic provided by the present invention has been determined to have the structure

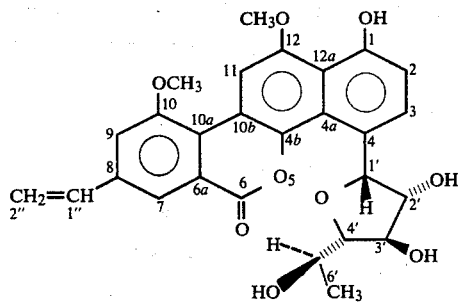

Anandimycin is a tan-yellow solid which decomposes at 177°–180° C. (does not decompose to a melt). It has a calculated molecular formula of $C_{27}H_{26}O_9$ and a molecular weight of 494.5.

Anandimycin is composed of the elements carbon, hydrogen and oxygen. Elemental analysis data is as follows:

Calculated for $C_{27}H_{26}O_9 \cdot H_2O$: C, 63.27; H, 5.50; Found: C, 63.20; H, 5.16

The infrared absorption spectrum of anandimycin when pelleted in KBr is shown in FIG. 1 of the accompanying drawings. Characteristic infrared absorption bands are exhibited at the following frequencies expressed in reciprocal centimeters: 3390 (broad, OH), 2980, 2950, 1715, 1628, 1615, 1595, 1565, 1515, 1495, 1455, 1440, 1385, 1345, 1300, 1255, 1195, 1170, 1140, 1075, 1055, 1015.

The ultraviolet absorption spectrum of anandimycin was determined in methanol (0.02888 g/l). Observed absorption maxima and absorptivities were as follows: Neutral and acid 246 (69.6), (s,278), 278 (63.4), (s,310, 320, 334, 350), 396 (24.7). Basic 220, (s,300), 405.

A proton magnetic resonance spectrum of anandimycin was determined with a Varian XL100 spectrometer operating at 100 MHz by dissolving about 1 mg of the antibiotic in 1 ml. of DMSO-d6 and using tetramethylsilane (TMS) as the internal reference. The nmr spectrum is reproduced as FIG. 2. Observed chemical shifts and pattern descriptions are as follows: $\delta$9.77 (s, 1H, phenol), 8.52 (s, 1H, C11-H), 8.08 (d, 1H, J=9 Hz, C2-H), 8.03 (d, 1H, J$\approx$2 Hz, C9-H), 7.79 (d, 1H, J$\approx$2 Hz, C7-H), 7.00 (dd, 1H, $J_1$=17 Hz, $J_2$=11 Hz, C1″-H), 6.98 (d, 1H, J=9 Hz, C3-H), 6.23 (d, 1H, J=5 Hz, C1′-H), 6.18 (d, 1H, J=17 Hz, C2″-Ht), 5.50 (d, 1H, J=11 Hz, C2″=Hc), 5.08 (d, 1H, J=5 Hz), 4.83 (d, 1H, J=5 Hz), 4.66 (m, 1H, C2′ H), 4.52 (d, 1H, J=7 Hz), 4.25 (s, 3H, OCH3), 4.20 (s, 3H, OCH3), 3.90 (m, 1H, C5′-H), 3.52 (dd, 1H, $J_1$=5 Hz $J_2$=7 Hz, C4′-H), 1.27 (d, 3H, J=7 Hz, C6′-H's).

A carbon-13 nuclear magnetic resonance spectrum of anandimycin was determined with a Varian XL-100 spectrometer operating at 25 MHz by dissolving about 80 mg. of the antibiotic in one ml. of DMSO-d6 and using TMS as the internal reference. Observed chemical shifts and assignments are as follows:

| Line (ppm) | Assignment |
|---|---|
| 159.2 | C6 |
| 157.0 | C10 |
| 152.3 | C12 |
| 151.5 | C1 |
| 142.0 | C4b |
| 138.3 | C8 |
| 135.0d | C1″ |

-continued

| Line (ppm) | Assignment |
| --- | --- |
| 128.7d | C3 |
| 125.8 | C4 |
| 123.4 | C4a |
| 122.7 | C10a |
| 121.9 | C6a |
| 118.8d | C7 |
| 116.8d | C2" |
| 114.6 | C12a |
| 114.2t | C9 |
| 112.5 | C10b |
| 111.7d | C2 |
| 101.2d | C11 |
| 85.6d | C1' |
| 80.6d | C2' |
| 78.7d | C3' |
| 78.5d | C4' |
| 66.3d | C5' |
| 55.5q | C12 OMe |
| 56.1q | C10 OMe |
| 20.1q | C6' |

When subjected to high pressure liquid chromatography under the following conditions, anandimycin exhibits the *k' values shown below:

Instrument:
 Waters Associates, Inc. Model M-6000A Solvent Delivery System; Waters Model U6K injector with 2 ml loop Column:
 μ-PORASIL prepacked column (Waters Associates, Inc. 3.9 mm 1D×30 cm., 10μ particle size, surface area 400 M²/g)

$$*k' = \frac{\text{elution volume of peak of interest} - \text{void volume of column}}{\text{void volume of column}}$$

Mobile Phase:
 (A) methyl t-butyl ether:acetone:water (98:2:0.4 v/v)
 (B) hexane:ethyl acetate:isopropanol:water (30:70:3:0.4 v/v)

Flow Rate:
 2 ml/min.

Detector:
 Waters Associates, Inc. Model 440 UV Detector; Schoeffel Model SF 770 Spectroflow monitor detector-365 nm for solvent system A, 365 nm and 254 nm for solvent system B k' Values:
 Mobile Phase A-1.4
 Mobile Phase B-1.35

Anandimycin has been discovered by the present inventors to be a minor component of the fermentation of *Streptomyces anandii* subsp. *araffinosus* strain C-22437 (ATCC 31431) disclosed in copending U.S. patent application Ser. No. 194,202 filed Oct. 6, 1980, now U.S. Pat. No. 4,301,248. That earlier application describes fermentation and isolation procedures for production of rachelmycin, now determined to be identical with antibiotic CC-1065 disclosed in U.S. Pat. No. 4,169,888. There is no disclosure in the prior application of the coproduction and/or isolation of anandimycin during fementation and recovery of rachelmycin.

Preparation of the anandimycin antibiotic according to the process of the present invention is described in detail below.

The Microorganism

The anandimycin-producing strain C-22,437 was isolated from a Katpadi, Madras, India soil sample and deposited in the American Type Culture Collection under the accession number ATCC 31431.

Strain C-22,437 (ATCC 31431)

Strain C-22,437 forms abundant aerial mycelium and develops aerial spore chains which show generally open spirals with several turns. Also found are short spore chains in hooked or looped shapes as well as spore chains in a closed irregular spiral at the tip. The spore chains are formed on monopodially branched sporophores and contain 10–50 spores in a chain. The spores are oval to cylindrical in shape and have a smooth surface. The aerial mycelium and spore chains are predominantly formed on Czapek's sucrose-nitrate agar, yeast extract-malt extract agar and Bennett's agar.

Some spore chains in coalesced spirals are filled with soft blackish material and develop into black moist globules. The globular spore masses appear to originate at the tip of the sporophore or at the intercalary site of the spore chain and are 5–10μ in diameter. The globules are predominantly formed on yeast extract-malt extract agar. Sclerotic granules which are oval in shape and 5–15μ in diameter are also formed in the substrate mycelium. The substrate mycelium is well-developed, branched and not fragmented.

The cell wall contains LL-diaminopimelic acid and glycine as diagnostic components. The whole cell hydrolyzate contains no diagnostic sugar.

Strain C-22,437 grows moderately on both nutritionally rich organic media and chemically defined media. The mass color of aerial mycelium is brownish gray on Czapek's sucrose-nitrate agar, yeast extract-malt extract agar, oatmeal agar, glycerol-asparagine agar and tyrosine agar, and is light gray on inorganic salts-starch agar. Melanoid pigments are produced on Czapek's sucrose-nitrate agar, tryptone-yeast extract broth, yeast extract-malt extract agar and tyrosine agar. Nonmelanoid pigments are not produced. The cultural characteristics of strain C-22,437 are shown in Table 4.

TABLE 4

Cultural Characteristics of Strain C-22,437

| | |
| --- | --- |
| Czapek's agar (Sucrose-nitrate agar) | G: Abundant<br>R: Dark grayish reddish brown (No. 47)<br>A: Abundant, brownish gray (No. 64) later partially grayish pink (No. 8)<br>D: Dark grayish reddish brown (No. 47) |
| Tryptone-yeast extract broth (ISP No. 1) | G: Moderate, surface-ring growth and sedimented cell mass<br>D: Dark brown (No. 59) |
| Yeast extract-malt extract agar (ISP No. 2) | G: Abundant<br>R: Dark grayish brown (No. 62)<br>A: Abundant, brownish gray (No. 64) and light gray (No. 264)<br>D: Moderate brown (No. 58) |
| Oatmeal agar (ISP No. 3) | G: Poor<br>R: Brownish orange (No. 54)<br>A: Restricted, light brownish gray (No. 63)<br>D: Light yellowish brown (No. 76) |
| Inorganic salts-starch agar (ISP No. 4) | G: Poor<br>R: Light grayish yellowish brown (No. 79)<br>A: Scant, white later light gray (No. 264)<br>D: None |

TABLE 4-continued
Cultural Characteristics of Strain C-22,437

| | |
|---|---|
| Glycerol-asparagine agar (ISP No. 5) | G: Moderate<br>R: Light reddish brown (No. 42)<br>A: Very limited formation, white later light brownish gray (No. 63)<br>D: None |
| Peptone-yeast extract-iron agar (ISP No. 6) | G: Moderate<br>R: Light grayish brown (No. 60)<br>A: None<br>D: Moderate brown (No. 58) |
| Tyrosine agar (ISP No. 7) | G: Abundant<br>R: Grayish brown (No. 61)<br>A: Scant, partial formation, yellowish gray (No. 93) later brownish gray (No. 64)<br>D: Light brownish gray (No. 63) |
| Glucose-ammonium-salts agar | G: Moderate<br>R: Light brownish gray (No. 63)<br>A: Moderate, light gray (No. 264)<br>D: None |
| Bennett's agar | G: Abundant<br>R: Light brown (No. 57) later dark brown (No. 59)<br>A: Abundant, brownish gray (No. 64), partially pale yellowish pink (No. 31) |

Cultivation: 28° C. for 3 weeks
G: Growth, R: Reverse, A: Aerial mycelium, D: Diffusible pigment
Color names were assigned according to "ISCC-NBS Centroid Color Charts", published by U.S. Department of Commerce National Bureau of Standards, Washington, D.C. 20234

Strain C-22,437 grows in the range of 20° to 45° C. but does not grow at 10° and 50°. It does not produce nitrite from nitrate. Gelatin is liquified late. It has considerable tolerance to sodium chloride.

D-Glucose, D-xylose, L-arabinose, D-fructose, D-galactose, D-mannitol, inositol and sucrose are utilized for growth. L-Rhamnose and raffinose are not utilized. The physiological characteristics and carbon utilization are shown in Tables 5 and 6, respectively.

TABLE 5
Physiological characteristics of Strain C-22,437

| | |
|---|---|
| Growth temperature: | Growth from 20° to 45° C. No growth at 10° and 50° C. |
| Hydrogen sulfide from: L-cysteine | Strongly positive |
| Nitrite from nitrate: | Negative (both in organic medium and chemically defined medium) |
| Reactions on milk: | No distinct reactions |
| Gelatin liquefaction: | Liquefied late |
| Starch hydrolysis: | Positive |
| Tolerance to sodium-chloride: | Resistant: Growth at 8% NaCl but no growth at 10% NaCl |

(Cultivation: 28° C.)

TABLE 6
Carbon Utilization of Strain C-22,437

| | | | |
|---|---|---|---|
| Glycerol | + | Melibiose | |
| D-Arabinose | | Trehalose | + |
| L-Arabinose | + | Raffinose | - |
| D-Xylose | + | D(+)-Melezitose | + |
| D-Ribose | + | Soluble starch | + |
| L-Rhamnose | - | Dulcitol | - |
| D-Glucose | + | Inositol | + |
| D-Galactose | + | D-Mannitol | + |
| D-Fructose | + | D-Sorbitol | |
| D-Mannose | + | Salicin | + |
| L(-)-Sorbose | - | Cellulose | - |
| Sucrose | + | Chitin | + |
| Lactose | + | Keratin | + |
| Cellobiose | + | | |

Observation after incubation at 28° C. for 2 weeks
Basal medium: Pridham and Gottlieb's mineral salts The morphological, cultural and physiological characteristics as well as the chemical composition of cells indicate that strain C-22,437 is a species of the genus Streptomyces. When characteristics of strain C-22,437 were compared with those of known species of Streptomyces described in the literature, it appeared most similar to *Streptomyces anandii*. Accordingly, strain C-22,437 has been named *Streptomyces anandii* subsp. *araffinosus* since it differs from *Streptomyces anandii* in not utilizing raffinose.

It is to be understood that the present invention is not limited to use of the particular strain C-22,437 or to organisms fully answering the above description. It is especially intended to include other anandimycin-producing strains or mutants of the said organism which can be produced from the described organism by known means such as x-radiation, ultraviolet radiation, treatment with nitrogen mustards, phage exposure, and the like.

Production of the Antibiotic

Anandimycin is produced by cultivating *Streptomyces anandii* subsp. *araffinosus* strain C-22,437 (ATCC 31431), or a mutant thereof, in a conventional nutrient medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts surface cultures and bottles may also be used. The general procedures used for fermentation of other actinomycetes are applicable to the present invention.

The nutrient medium should contain an appropriate assimilable carbon source such as lactose, glycerol, sucrose, glucose, mannose, fructose, corn starch, etc. As nitrogen sources, ammonium chloride, ammonium sulfate, urea, ammonium nitrate, sodium nitrate, etc. may be used either alone or in combination with organic nitrogen sources such as peptone, meat extract, yeast extract, corn steep liquor, soybean powder, cotton seed flour, etc. There may also be added if necessary nutrient inorganic salts to provide sources of sodium, potassium, calcium, ammonium, phosphate, sulfate, chloride, bromide, carbonate, zinc, magnesium, manganese, cobalt, iron and the like.

Production of the anandimycin antibiotic can be effected at any temperature conducive to satisfactory growth of the producing organism, e.g. 20°-45° C., and is conveniently carried out at a temperature of around 27°-32° C. Ordinarily, optimum production is obtained after incubation periods of about 3-11 days. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium.

Isolation of Anandimycin

When fermentation is complete, anandimycin is recovered from the culture medium and isolated in a substantially pure form according to the multistep procedure illustrated in the following flowchart.

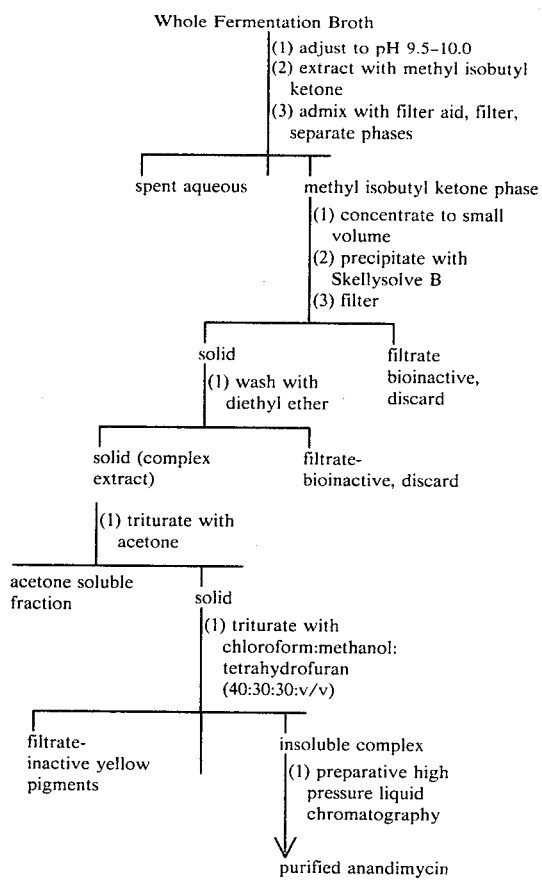

To elaborate on the flowchart, the whole broth from fermentation of *Streptomyces anandii* subsp. *araffinosus* strain C-22,437 is first extracted with a water-immiscible organic solvent. Intermediate polarity solvents such as ethyl acetate, amyl acetate and methyl isobutyl ketone are preferred with methyl isobutyl ketone being most preferred in view of its low volatility and, consequently, reduced loss during subsequent filtration of the mycelial mat. The antibiotic complex (including anandimycin) extracts best under slightly alkaline conditions (pH 9.5–10) with poor extraction being noted under acidic conditions. Filter aid is preferably added to the extraction mixture and the mixture then filtered to remove insolubles. After filtration, the organic phase is separated from the extraction mixture filtrate, concentrated to a small volume and diluted with an appropriate antisolvent to precipitate out the antibiotic complex as a yellow solid. Suitable antisolvents can be determined by simple test and include such organic non-solvents for anandimycin as diethyl ether, benzene and liquid aliphatic hydrocarbons such as n-hexane, n-heptane or Skellysolve B (tradename of Skelly Oil Co. for isomeric hexanes).

The solids obtained from extraction of the whole broth are next washed with diethyl ether to remove any lard oils and antifoams used in the fermentation. The ether-washed solids contain what appears to be a group of closely related yellow pigments, none of which has been shown to have antitumor activity. These yellow pigments do show antibiotic properties and are the major components of the solid recovered from the fermentation extract. Experience has demonstrated that separation of these impurities from the minor component of interest (i.e. anandimycin) using silica gel chromatography is not possible because the pigments typically crystallize on the silica gel surface, thereby leading to smearing effects which prevent any meaningful separation. To remedy this problem a simple organic solvent trituration scheme was developed which effects a gross separation of the yellow pigments and another class of antitumor agents produced by strain C-22,437 (rachelmycin) from anandimycin on the basis of differential solubility. The trituration process is carried out in two steps, each of which results in selective dissolution of impurities and hence separation from anandimycin, which is insoluble throughout the process. The first step involves trituration of the extraction solids with acetone. The resulting filtrate contains another antitumor substance which is active in the lysogenic bacteria induction assay and the P388 mouse tumor system (rachelmycin). The insoluble solid from the acetone trituration contains the yellow pigments along with a complex of anandimycin and another similar compound. The second phase of the process involves trituration with a ternary organic solvent system 40:30:30($v/v$) chloroform:methanol:tetrahydrofuran. The soluble fraction contains the yellow pigments. The insoluble fraction contains the enriched anandimycin mixture (a mixture of anandimycin and a substance structurally related to anandimycin but biologically inactive). Substantially pure anandimycin is separated from the enriched mixture using high pressure liquid chromatography on silica gel as described in more detail below.

Analytical high pressure liquid chromatography, *Bacillus subtilis* zone of inhibition, lysogenic bacterial induction and P388 mouse tumor assays are used throughout the above-described separation processes to monitor relative levels of anandimycin and co-produced substances.

Resolution of the anandimycin mixture (insoluble fraction from chloroform:methanol:tetrahydrofuran trituration) is accomplished through the use of high pressure liquid chromatography techniques employing silica gel columns. The analytical solvent system routinely used is hexane:ethyl acetate:isopropanol (30:70:3$v/v$) along with 0.1 to 0.4 part water depending on the relative activity state of the silica gel surface in the column being used. If tailing effects are observed, then typically one increases the water content of the solvent system within the 0.1–0.4 part range to improve peak symmetry, thereby permitting a more quantitative analysis.

High pressure liquid chromatographic separation of the anandimycin mixture is possible only on a limited scale (200–300 mg) due to a relatively low solubility of the mixture in the developing solvent system. The preparative solvent system is ethyl acetate:isopropanol:water (87:13:0.5$v/v$). Shave-recycle methodology is used to effect separation of anandimycin from the structurally related component (later determined to have the structure

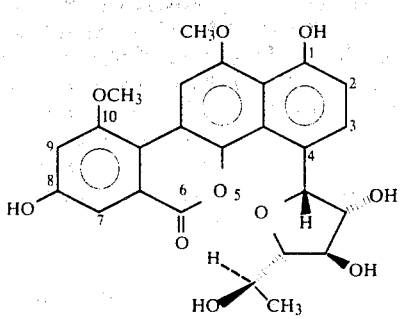

and to be biologically inactive). A shave-recycle method involves increasing the effective silica gel column length through the employment of continuous multiple pass chromatography of the anandimycin-component II band. The separation was achieved in two stages. Initial chromatography gave anandimycin enriched to 70-85% purity. Accumulated solids are rechromatographed to yield material of >90% purity.

In view of the poor solubility of anandimycin and component II in solvents generally useful for preparative chromatography, an alternate procedure was attempted. The anandimycin-component II mixture was acetylated and a preparative scale separation of the peracetylated mixture attempted. The solubility of the acetylated compounds was greatly improved and separation of the acetates on a larger scale proceeded smoothly. Attempted saponification of anandimycin tetraacetate, however, gave only a 30% recovery of anandimycin.

Structure of Anandimycin

The structure of anandimycin has been determined by a combination of x-ray analysis and nmr spectroscopy. Neither anandimycin nor component II gave crystals suitable for x-ray analysis. The pure acetates were similarly unsuitable. It was observed, however, that recrystallization of an ~1:1 mixture of anandimycin and component II gave larger crystals than either compound alone. Since nmr spectroscopy had shown that anandimycin and component II were very similar (differing only in that anandimycin had an aromatic vinyl function in place of a phenol in component II), it was reasoned that x-ray crystallography might result in a partial structure of those parts of the molecule which were common to both structures. Consequently, single crystal x-ray crystallography resulted in the structures for anandimycin and component II shown above. The absolute configuration of anandimycin remains to be determined.

Biological Activity Data

The in vitro minimum inhibitory concentrations (MIC) of anandimycin were determined against a variety of microorganisms using the standard tube dilution procedure. The results (along with those for component II) are shown in the table below.

| | Minimum Inhibitory Concentration (µg/ml) | |
|---|---|---|
| Organism | Anandimycin | Component II |
| Str. pneumoniae 9585 | 0.13 | 0.25 |
| Str. pyogenes 9604 | 0.13 | 0.5 |
| Staph. aureus 9587 | 0.06 | 0.13 |
| Staph. aureus (penicillin-resistant) 9606 | 0.25 | 0.5 |

-continued

| | Minimum Inhibitory Concentration (µg/ml) | |
|---|---|---|
| Organism | Anandimycin | Component II |
| Str. faecalis 20,588 | 0.016 | 0.13 |
| E. coli 15119 | >63 | >63 |
| E. coli 20341-1 | >63 | >63 |
| K. pneumoniae 15130 | >63 | >63 |
| Pr. mirabilis 9900 | >63 | >63 |
| Pr. vulgaris 21559 | 2 | >63 |
| Ser. marcescens 20019 | >63 | >63 |
| Ent. cloacae 9659 | >63 | >63 |
| Ps. aeruginosa 9843A | >63 | >63 |

Anandimycin is completely devoid of ILB activity at a maximum concentration of 1.6 µg/ml. Above this level, the antibiotic is toxic to the host organism (E. coli).

Anandimycin was also tested against the transplantable mouse tumor P-388 leukemia. The methodology used generally followed the protocols of the National Cancer Institute (Cancer Chemotherapy Rep., Part 3, 3, 1-103 (1972). The essential experimental details are given at the bottom of the following table. Two different dose regimens are tested: single dose on day 1 and three doses given on days 1, 5 and 9. The optimal dose was 64 mg/kg. single dose.

| Effect of Anandimycin on P-388 Leukemia | | | | | |
|---|---|---|---|---|---|
| Compound | Treatment Schedule | Dose, IP mg/kg/inj. | MST days | Effect MST % T/C | AWC gm. Day 4 | Survivors Day 5(30) |
| Anandimycin | d.1 | 64 | 14.5 | 161 | −0.3 | 6/6 |
| | | 32 | 13.0 | 144 | −0.6 | 6/6 |
| | | 16 | 11.0 | 122 | −0.6 | 6/6 |
| | | 8 | 11.5 | 128 | −0.2 | 6/6 |
| | | 4 | 10.0 | 111 | −0.9 | 6/6 |
| | | 2 | 10.0 | 111 | −0.2 | 5/5 |
| | | 1 | 9.0 | 100 | −0.1 | 6/6 |
| | | 0.5 | 9.0 | 100 | −0.1 | 6/6 |
| Anandimycin | d.1,5&9 | 16 | 13.0 | 144 | 0 | 5/5 |
| | | 8 | 13.5 | 150 | +0.2 | 6/6 |
| | | 4 | 10.5 | 117 | +0.7 | 6/6 |
| | | 2 | 9.0 | 100 | +0.2 | 6/6 |
| | | 1 | 9.0 | 100 | +0.6 | 6/6 |
| | | 0.5 | 9.0 | 100 | −0.1 | 6/6 |
| Control | Saline | | 9.0 | — | 0 | 10/10 |

Tumor inoculum: $10^6$ ascites cells implanted ip
Host: $CDF_1$ ♀ mice
Evaluation: MST = median survival time
Effect: % T/C = (MST treated/MST control) × 100
Criteria: % T/C ≧ 125 considered significant anti-tumor activity
Tox: > 4/6 mice alive on day 5
AWC = average weight gain (treated-control) in grams (on day 4)

As indicated by the antimicrobial and mouse tumor data provided above, anandimycin is useful as an antimicrobial agent (e.g. against gram-positive pathogenic bacteria such as Str. pneumoniae, Str. pyogenes, Str. faecalis and Staph. aureus) and as an antitumor agent for inhibition of mammalian malignant tumors such as P-388 leukemia.

Anandimycin may be employed in the form of a pharmaceutical composition containing an effective antimicrobial or tumor-inhibiting amount of anandimycin in combination with an inert pharmaceutically acceptable carrier or diluent. Such compositions may optionally contain other active antimicrobial or antitumor agents and may be made up in any pharmaceutical form appropriate for the selected route of administration. Examples of such compositions include solid compositions for oral administration such as tablets, capsules, pills, powders and granules, liquid compositions for oral administration such as solutions, suspensions, syrups or elixers and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antimicrobial agent, the anandimycin or pharmaceutical composition thereof is administered so that the concentration of active ingredient is greater than the minimum inhibitory concentration for the particular organism being treated. For use as an antitumor agent, optimal dosages and regimens of anandimycin for a given mammalian host can be readily ascertained by those skilled in the art. It will of course be appreciated that the actual dose of anandimycin used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are provided for illustrative purposes only and are not intended to limit the scope of the invention. Skellysolve B is a commercially available petroleum solvent. (Skelly Oil Co.) comprising isomeric hexanes and having a boiling point of 60°–69° C. $\mu$ PORASIL is a fully porous silica adsorbent used in liquid chromatography and manufactured by Waters Associates, Inc., Milford, Mass. Unless otherwise indicated, all temperatures below are in degrees Centigrade.

EXAMPLE 1

Fermentation of Anandimycin

A. Shake-flask Fermentation

*Streptomyces anandii* subsp. *araffinosus* strain C-22,437 was maintained and transferred in test tubes on agar slants of yeast extract-malt medium consisting of 4 g glucose, 4 g. yeast extract, 10 g. malt extract and 20 g. agar made up to one liter with distilled water. With each transfer the agar slant culture was incubated for seven days at 27° C. To prepare an inoculum for the production phase the surface growth from a slant culture was transferred to a 500 ml. Erlenmeyer flask containing 100 ml of sterile medium consisting of 30 g. glucose, 30 g. soy flour and 3 g. CaCO₃ made up to one liter with distilled water. This vegetative culture was incubated at 27° C. for 48 hours on a Gyrotory tier shaker (Model G-53, New Brunswick Scientific Co., Inc.) set at 230 rev./min describing a circle with a 5.1 cm diameter. Four ml of vegetative culture was transferred to a 500 ml Erlenmeyer flask containing 100 ml of sterile production medium consisting of 50 g. glucose, 20 g. soy flour, 5 g. Fermo 30 yeast (Yeast Products, Inc. Paterson, N.J.), 5 g. washed brewers' yeast, 5 g. Maggi yeast extract (The Nestle Co., White Plains, N.Y.), 0.25 g (NH$_4$)$_2$SO$_4$ and 3 g. CaCO$_3$ made up to one liter with distilled water. The production culture was incubated at 27° C. on a shaker such as used for the vegetative culture set at 210 rev./min for 240 hours at which time the culture contained anandimycin.

B. Tank Fermentation

For production of anandimycin in a tank fermentor, 380 liters of vegetative culture as described in Example 1A were transferred to a tank containing 3030 liters of medium consisting of 50 g. glucose, 20 g. soy flour, 5 g. Fermo 30 yeast, 5 g. yeast extract, 5 g. washed brewers' yeast, 0.25 g. (NH$_4$)$_2$SO$_4$ and 3 g. CaCO$_3$ made up to one liter with tap water. Temperature was maintained at 27° C., the air flow rate was 1400 liters/min, the back pressure was 1 atm. and the agitation rate was 155 rev./min. Polypropylene glycol was used to control foaming. The tank fermentation was terminated after 82 hours of incubation for isolation of anandimycin.

EXAMPLE 2

Isolation of Bioactive Complex from Fermentation Broth

A. Small Scale Isolation

Whole fermentation broth (8 liters) was adjusted from pH 7.9 to pH 9.5 with dilute aqueous sodium hydroxide and stirred vigorously with an equal volume of methyl isobutyl ketone for 20–30 min. The mixture was admixed with inert diatomaceous earth filter aid and filtered on a mat formed of the same material and under vacuum suction. The phases in the filtrate were separated, and the aqueous phase, except for a small sample reserved for bioassays, was discarded. The organic phase was evaporated under vacuum to a small volume (50–100 ml) and diluted with Skellysolve B to precipitate a dark yellow solid which was dried in vacuo to give 3.5 g of bioactive complex extract. Solids obtained from this method are typically active in the P388 mouse tumor system down to 0.4–0.8 mg/kg/day dosage.

B. Large Scale Isolation

Whole fermentation broth (3000 liters) at pH 8.0 was admixed with inert diatomaceous earth filter aid and filtered under vacuum. The filtrate was chilled at 0°–10° C. The mycelial/filter aid cake was extracted by recirculating 1000 liters of acetone through the mat filter under vacuum. The acetone extract was concentrated to an aqueous residue under reduced pressure which was combined with the chilled filtrate, adjusted to pH 9.5–10.0 with 10% sodium hydroxide, and stirred vigorously with a half volume of methyl isobutyl ketone. The phases were separated using continuous centrifugation (Centrico Inst. Corp., Model MEM-1256 centrifuge). The pH of the aqueous layer was checked and readjusted to pH 9.5–10.0 if necessary. Reextraction with an additional half volume of methyl isobutyl ketone was carried out as above. The spent aqueous was then discarded and the methyl isobutyl ketone extracts combined and vacuum concentrated at 0°–10° C. to a near oil and then diluted with 10–20 volumes of heptane or Skellysolve B to precipitate an orange-yellow tacky solid which weighed approximately 800 g. This tacky solid was washed with 10 liters of diethyl ether to remove approximately 100 g. of inactive oily material. The orange-yellow solid was dried in vacuo to yield approximately 700 g. of bioactive complex extract.

EXAMPLE 3

Solvent Trituration of the Bioactive Complex

A. Small Scale Purification

Crude bioactive complex extract (15 g) as extracted in Example 2 from whole broth was triturated with 1.5 liters acetone using magnetic stirring and sonication aids. The thoroughly triturated solution/suspension was filtered under vacuum using a suitable medium porosity sintered glass filter. The soluble fraction was evaporated to dryness to give 7.6 g of a dark tannish-red solid.

Analysis of this fraction has shown it to consist of a complex array of components including the antitumor agent rachelmycin which possesses both antibiotic and lysogenic bacterial induction activity. The insoluble fraction (7.4 g) is a yellow solid which by analysis contains yellow pigment and a mixture of anandimycin and a related component designated above as component II. Secondary processing of the 7.4 g yellow solid involves trituration with 1 liter of 40:30:30, chloroform/methanol/tetrahydrofuran ($^v/v$). Magnetic stirring and sonication procedures are used as with the acetone trituration. The resulting solution/suspension was filtered using a medium porosity sintered glass filter. Evaporation of the filtrate yielded 4.6 g of yellow pigment with only trace amounts of the anandimycin-component II mixture. The insoluble fraction was greenish-yellow in color, weighed 2.8 g, and was shown by HPLC analysis to contain enriched anandimycin-component II complex.

B. Larger Scale Purification

Crude bioactive complex extract (700 g) as extracted in Example 2 from whole broth obtained from a 3028 liter scale tank fermentation was triturated vigorously with two 5 liter portions of acetone using air driven mechanical overhead stirring devices. The resulting solution/suspension was filtered under vacuum using a large Buchner funnel. The combined filtrates were evaporated to dryness yielding 518 g of solid which contains the antitumor substance rachelmycin. The insoluble yellow solid, which weighed 120 g, was subsequently triturated with two 4 liter portions of 40:30:30, chloroform/methanol/tetrahydrofuran ($^v/v$). The combined filtrates were evaporated to dryness to yield 73.2 g of yellow pigment solids. The final insoluble greenish-yellow solid weighed 46.6 g. HPLC analysis of the latter solid confirmed the presence of anandimycin.

The bioactive complex extract used in Example 3 was evaluated in several TLC (thin layer chromatography) systems. Eventually, a chloroform:methanol:water (90:10:0.25 $^v/v$) solvent system was observed to afford the best resolution of the systems tested. At least 20 different components are resolved in the complex extract using this system. The anandimycin-component II complex is a single spot and is distinctly characterized by a bright yellow fluorescence under long wave light.

EXAMPLE 4

HPLC Separation of the Anandimycin-Component II Mixture

A. Analytical HPLC System

The HPLC apparatus used in this procedure consisted of a Waters Assoc. Model M-6000A Solvent Delivery System, a Waters Assoc. Model U6K injector with 2 ml loop. a $\mu$-Porasil prepacked column (Waters Assoc., 3.9 mm ID×30 cm, 10$\mu$ particle size, surface area 400 $M^2$/g), a Waters Assoc. Model 440 UV detector, a Schoeffel Model SF770 spectroflow monitor detector, and a Heath/Schlumberger strip chart recorder.

The solvent system developed for optimum analytical separation of the anandimycin-component II complex was 30:70:3:0.1, hexane/ethyl acetate/iso-propanol/water. The following separation parameters were observed:

$k'_{C_2*} = 1.35$,
$k'_{C_3**} = 1.90$,
$\alpha_{C_2,C_3} = 1.4$
*$C_2$ = anandimycin
**$C_3$ = component II Variability between different columns and in the same column over time with respect to activity results in $k'$ variability and sometimes adverse tailing effects. It was determined that when adverse tailing occurs, increasing the water concentration of the solvent system (between the range of 0.1–0.4 parts) served as a convenient remedy for this frequently observed problem. The water level in the solvent system should be kept to a minimum, however, in order to maximize the lifespan of ideal column activity after which extensive regeneration procedures are necessary to reactivate the silica gel surface.

The column effluents were monitored at UV-254 nm or 365 nm. Flow rate was typically 3.0–4.0 ml/min. Samples of 1–50 $\mu$g were generally injected. Relatively enriched anandimycin solids were dissolved in 10 percent methanol in tetrahydrofuran to approximately 1 mg/ml concentration for HPLC assay.

B. Preparative HPLC System

The column chamber of a Prep LC/System 500 apparatus (Waters Assoc., Inc., Milford, Mass.) was loaded with two PrepPak-500 silica gel columns and placed under a radial pressure of 40 atm. When a new PrepPak was being used for the first time, deactivation of the silica gel surface with a solvent system containing a high water concentration relative to the chromatographic solvent system was carried out. The deactivation procedure involves pumping a 5 liter volume of solvent through the columns at a flow rate of 200 ml/min wasting the first 2 liters of effluent, then recirculating on the remaining 3 liter volume for 30 min. In this method the deactivation solvent system is 90:10:1, ethyl acetate/methanol/water, which also is used as a routine post-chromatography column wash solvent.

The chromatographic solvent system employed in this method is 87:13:0.5, ethyl acetate/iso-propanol/water. Typically, 20 liters of this solvent mixture is prepared for one chromatographic process. Equilibration to this solvent system is effected by passing 5 liters through the PrepPak columns to waste and is evidenced by a stable refractive index baseline at a relative response setting of 20.

Load sample preparation involves saturation of 500 ml of chromatographic solvent with enriched anandimycin-component II mixture using sonication dispersal of the solid. Typical weight loads range from 100 mg to 300 mg. The maximum load weight achievable (within this range) is inversely related to the purity of the mixture with respect to anandimycin. For example, 2.3 g of anandimycin-component II-rich solid from the solvent trituration enrichment process is triturated with 500 ml of 87:13:0.5, ethyl acetate/iso-propanol/water with sonication. Filtration yielded 2.2 g of insolubles. The filtrate (100 mg) is pumped into the equilibrated Prep LC/System 500 via one of the solvent inlet ports, following which elution was begun from the main solvent reservoir through the other inlet. The effluent stream from the stream splitter, which diverts 1–2% of the main column effluent for detection purposes, was monitored using a UV detector (Schoeffel Instrument Corp., Spectroflow SF770) with the variable wavelength accessory set at 400 nm. The built-in refractive index detector was not a useful monitor of this chromatography presumably due to insensitivity.

The observed analytical separation factor ($\alpha = 1,4$) warranted a consideration of the application of shave-recycle methods during preparative chromatography. Direct application of the analytical solvent system to the preparative scale was characterized by unacceptable high retention and interband tailing which led to band mixing. To remedy this problem, the hexane was removed from the solvent system and the iso-propanol concentration increased to 13 parts in order to decrease retention and tailing effects. The resulting 87:13:0.5, ethyl acetate/iso-propanol/water, system was suitable for application of shave-recycle methodology in that band spreading during each pass was minimized. In the mechanism of recycle, the column effluent, instead of being directed to waste, is diverted to the suction side of the pump and pumped through the column bed again. In each recycle step the chromatographic column length is effectively increased resulting in higher resolution. Typical separations have involved 8-10 recycles. Resulting preparative fractions are assayed for relative anandimycin concentration using the abovementioned analytical HPLC system.

Parameters for the analytical and preparative HPLC separations are given below:

| Prep: | |
|---|---|
| Flow: | 200 ml/min |
| Solvent: | 87:13:0.5, ethyl acetate/iso-propanol/water |
| Detect: | UV at 400 nm |
| Chart Speed: | 0.2 in/min. |
| Column: | 2 silica PrepPaks |
| Load: | 100 mg enriched anandimycin-component II mixture |
| Anayltical: | |
| Flow: | 4.0 ml/min |
| Solvent: | 30:70:3:0.1, hexane/ethyl acetate/iso-propanol/water |
| Detection: | UV at 365 nm |
| Sensitivity: | 0.04 AUFS |
| Column: | µPorasil |
| Chart Speed: | 0.2 in/min. |

After fractions were assayed using analytical HPLC, work-up of composites involved evaporation to dryness under reduced pressure. Following is a description of the composites and weight recovered from the chromatographic process described above,

| Composite Fractions | Weight | Analytical HPLC Summary |
|---|---|---|
| 6,7,10,13,17,22,26,27,32–36 | 31.4 mg | ≧ 90 area percent anandimycin |
| 3–5,9,21,23,25,28,30,31,37,38 | 26.2 mg | anandimycin-component II mixture |
| 8,11,12,14–16,18–20,24,29,37 | 35.4 mg | component II-rich |

A total of 93 mg of solid weight was recovered, a 93% weight recovery.

Initial shave-recycle chromatography typically processed the anandimycin to at least 80–90 area percent purity as estimated from analytical HPLC. Solids of this purity were accumulated and processed a final time, using the shave-recycle method, to obtain anandimycin of at least 95 area percent purity.

We claim:
1. A process for producing the antitumor antibiotic anandimycin having the formula

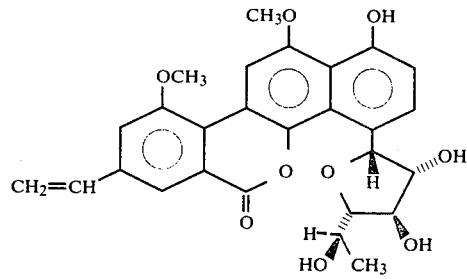

which comprises cultivating an anandimycin-producing strain of Streptomyces anandii subsp. araffinosus having the identifying characteristics of ATCC 31431, or a mutant thereof, in an aqueous nutrient medium under submerged aerobic conditions until a substantial amount of anandimycin is produced by said organism in said culture medium and recovering the anandimycin from the culture medium substantially free of substances co-produced therewith.

* * * * *